United States Patent [19]
Zhang

[11] Patent Number: 5,721,189
[45] Date of Patent: Feb. 24, 1998

[54] TREATMENT TO IMPROVE THE DURABILITY OF A HYDRODECHLORINATION CATALYST AND CATALYST

[75] Inventor: Zongchao Zhang, Northvale, N.J.

[73] Assignee: Akzo Nobel N.V., Arnhem, Netherlands

[21] Appl. No.: 755,759

[22] Filed: Nov. 21, 1996

Related U.S. Application Data

[63] Continuation-in-part of Ser. No. 568,710, Dec. 7, 1995, abandoned, which is a continuation-in-part of Ser. No. 647,091, May 9, 1996, abandoned.

[51] Int. Cl.$^6$ .................. B01J 27/13; C07C 1/00
[52] U.S. Cl. .................. 502/504; 585/641; 585/733; 208/262.1; 502/503; 502/226; 502/229; 502/230; 502/326; 502/339
[58] Field of Search .................. 502/501, 502, 502/503, 504, 327, 229, 230, 226, 326, 333, 334, 339; 585/641, 733; 208/262.1

[56] References Cited

U.S. PATENT DOCUMENTS

| | | | |
|---|---|---|---|
| 4,374,047 | 2/1983 | Bozon et al. | 252/472 |
| 4,863,890 | 9/1989 | Koll | 502/230 |
| 4,980,324 | 12/1990 | Kellner et al. | 502/36 |
| 5,057,470 | 10/1991 | Kellner | 502/35 |
| 5,105,032 | 4/1992 | Holbrook | 570/101 |
| 5,474,964 | 12/1995 | Wu et al. | 502/326 |
| 5,625,110 | 4/1997 | Schoedel et al. | 585/641 |

FOREIGN PATENT DOCUMENTS

| | | | |
|---|---|---|---|
| 535619 | 4/1993 | European Pat. Off. | B01J 29/38 |

OTHER PUBLICATIONS

J. Hancsók et al., "The Effect of Platinum–Dispersion on the Isomerization of N–Pentane", Hungarian Journal of Industrial Chemistry, vol. 17, pp. 131–137 (1989).

A. Bellare et al., "Evolution of Bimodal Distributions in the Sintering of Model Supported Metal Catalysts", Journal of Catalysis, vol. 117, pp. 78–90 (1989).

I. Sushumna et al., "Events Observed and Evidence for Crystallite Migration in Pt/Al$_2$O$_3$ Catalysts", Journal of Catalysis, vol. 109, pp. 433–462 (1988).

D.J. Smith, "The Characterisation of a Model Platinum/Alumina Catalyst by High–Resolution Electron Microscopy", Journal of Catalysis, vol. 81, pp. 107–118 (1983).

R.W. McCabe et al., "The Passivating Oxidation of Platinum", Journal of Catalysis, vol. 114, pp. 354–367 (1988).

Chemical Abstracts, vol. 118, 83281w (1993).

*Primary Examiner*—Glenn Caldarola
*Assistant Examiner*—In Suk Bullock
*Attorney, Agent, or Firm*—Richard P. Fennelly; Louis A. Morris

[57] ABSTRACT

The durability of a supported noble metal hydrodechlorination catalyst can be improved by (1) treating the supported catalyst, which comprises support and catalytic noble metal, with a non-elemental halide compound, which is not a mineral acid (such as an alkali metal halide, an ammonium halide, an alkaline earth metal halide, and/or a halogenated hydrocarbon); and (2) then using the treated catalyst in a hydrodechlorination reaction. Suitable treatment compounds include ammonium chloride, lithium chloride, or a chlorinated hydrocarbon. The treated catalyst is a novel composition of matter comprising at least one platinum group metal supported by an oxidic support wherein the metal, which is in the zero valent state, predominantly resides adjacent the surface of the support and is predominantly visible under a microscope having a resolution of about 5 Å.

13 Claims, 2 Drawing Sheets

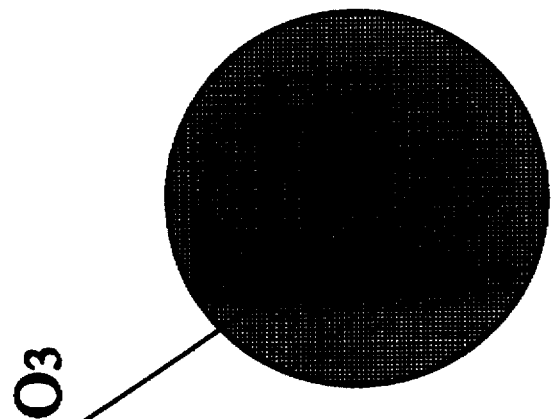
FIG. 1A Homogeneous Distribution
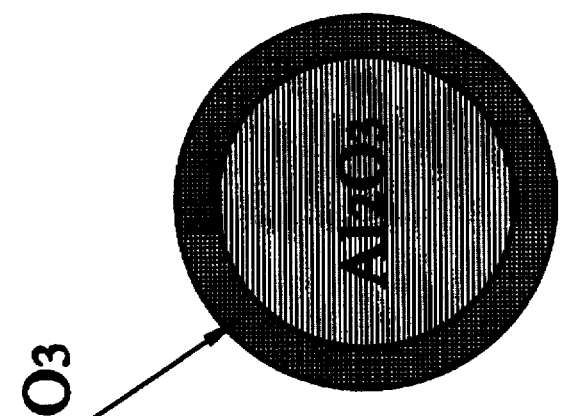
FIG. 1 Egg-Shell Distribution

TREATMENT TO IMPROVE THE DURABILITY OF A HYDRODECHLORINATION CATALYST AND CATALYST

This is a continuation-in-part of U.S. Ser. No. 08/568,710, filed Dec. 7, 1995, now abandoned, which, in turn, is a continuation-in-part of Ser. No. 08/647,091, filed May 9, 1996.

BACKGROUND OF THE INVENTION

Various techniques are known for the regeneration or treatment of hydrodehalogenation or hydrodechlorination catalysts. The following are some examples of disclosures that are deemed to be relevant to the present invention.

U.S. Pat. No. 4,980,324 to C. S. Kellner et al. discloses the regeneration and/or activation a noble metal catalyst by the use of a fluorohalocarbon and/or a fluorohydrocarbon. In more recent U.S. Pat. No. 5,057,470 C. S. Kellner advocates the contacting of a hydrodehalgenation catalyst with an atmosphere comprising chlorine gas at elevated temperature for a time which is sufficient to improve the catalytic activity of the catalyst.

U.S. Pat. No. 4,374,047 of A. Bozon et al. teaches the pre-loading of a porous catalyst carrier with an aqueous solution of ammonium chloride prior to applying a coating containing platinum and/or palladium to the surface of the treated porous catalyst carrier.

More recent U.S. Pat. No. 5,105,032 to M. T. Holbrook et al. indicates that a supported platinum catalyst that has been subjected to chloride pre- treatment, can be used in the hydrodechlorination of carbon tetrachloride to produce chloroform and methylene chloride. The types of chloride treatment that are disclosed by this patent include treatment of the catalyst with hydrochloric acid and chlorine at an elevated temperature.

The regeneration of a deactivated catalyst which is useful in the production of aromatic compounds, rather than as a hydrodechlorination catalyst, is described in European Patent Publication No. 535,619. In this patent, a deactivated catalyst containing a zeolite and a noble metal from Group VIII of the Periodic Table is treated with a variety of halogen and halogen-containing compounds including such species as hydrogen chloride, ammonium chloride, and ammonium fluoride.

Certain descriptions in the published prior art dealing with hydrodechlorination catalysts comprising platinum group metal(s) supported by an oxidic support indicate that the platinum group metal is homogeneously distributed on and through the support. Examples of such disclosures include: D. J. Smith et al., Journal of Catalysis 81, 107–118 (1983); I. Sushumna et al., Journal of Catalysis 109; 433–462 (1988); R. W. McCabe et al., Journal of Catalysis 114, 354–367 (1988); A. Bellare et al., Journal of Catalysis 117, 78–90 (1989); and J. Hancsók et al., Hungarian Journal of Industrial Chemistry, Vol. 17, 131–137 (1989). Commercially available catalysts, however, can be obtained which comprise at least one platinum group metal supported by an oxidic support wherein the metal, which is in the +1 valent state, predominantly resides adjacent the surface of the support (so as to produce a so-called "egg-shell" appearance for the distribution of the metal if the support containing it is broken and viewed in cross-section. The metal component in such a catalyst is not predominantly visible under a microscope having a resolution of about 5 Å since a predominant portion of its metal species have a particle size well below about 5 Å.

SUMMARY OF THE PRESENT INVENTION

The present invention relates to a process for enhancing the durability of a supported noble metal hydrodechlorination catalyst. The process comprises treating the supported catalyst, which comprises support and catalytic noble metal, with a non-elemental halide compound, which is not a mineral acid. An example of a suitable compound is ammonium chloride. The treated catalyst is then utilized in a hydrodechlorination reaction which will demonstrate the greater durability of the catalyst as measured by retention of desired performance for a longer period of time as compared to an untreated catalyst.

The treated catalyst of the present invention is also a novel composition of matter comprising at least one platinum group metal supported by an oxidic support wherein the metal, which is in the zero valent state, predominantly resides adjacent the surface of the support and is predominantly visible under a microscope having a resolution of about 5 Å.

BRIEF DESCRIPTION OF THE DRAWINGS

The present invention, is further understood by reference to the Drawings which form a part of the present application wherein:

FIG. 1 and 1A are schematic views, in cross-section of the catalyst of the present invention, showing the "egg-shell" distribution of platinum particulates, and a conventional catalyst showing the homogeneous distribution of platinum particulates.

DESCRIPTION OF DETAILED EMBODIMENTS

Figure 2:
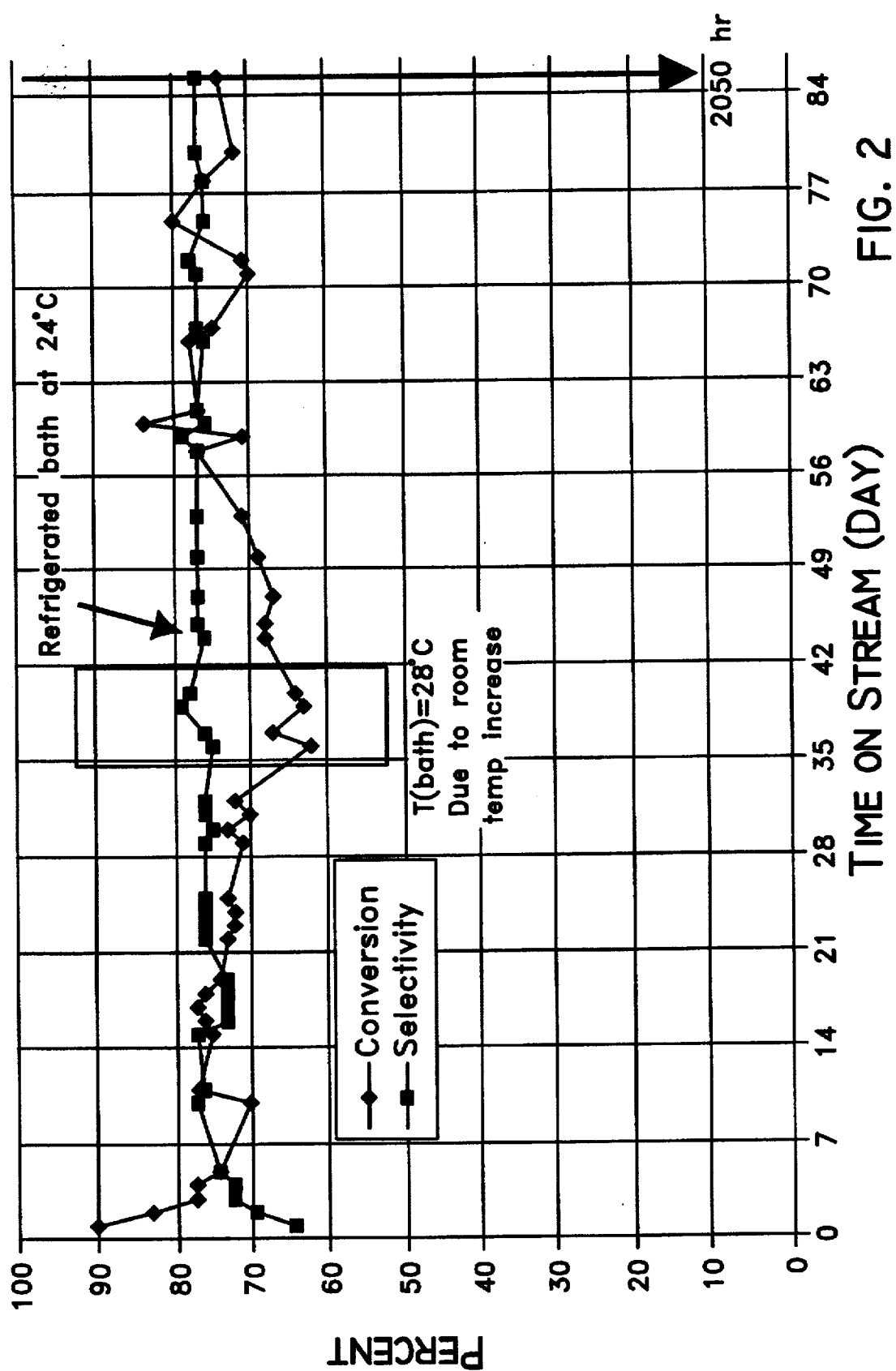
FIG. 2 which illustrates the results of a durability test of the catalyst of the present invention, as more fully described in Example 11 hereinbelow.

The present invention is directed to a process for enhancing the durability of a supported noble metal hydrodechlorination catalyst. By, the term "durability" is meant that there is a substantial retention of activity, over time, as the catalyst is used in its intended manner in a hydrodechlorination reaction. For example, a conventional catalyst of the type to be described herein, which is not treated in accordance with the present invention will go from an initial conversion rate of about 90%, initially, to about 2% in about one half hour time. In contrast, the current invention, in a most preferred embodiment, will allow such a catalyst to stay at about 85% conversion for at least about one week.

The type of catalyst to which the present invention relates is a supported catalyst which comprises both support and catalyst noble metal. It is well within the skill of persons of ordinary skill in the art familiar with prior art hydrodechlorination catalysts to select appropriate support materials and appropriate catalytic noble metals for use in the fabrication of appropriate supported catalysts which can be treated with the present invention.

The type of support which is preferred for purposes of the present invention, is an oxidic support. Representative supports of this type include silica, alumina, zirconia, titania, and the like. It is preferably a pelletized support.

The type of catalytic metal which forms the other component of the catalyst which is to be treated in accordance with the present invention, is preferably a Group VIII noble metal such as platinum, palladium, or mixtures thereof. It is generally present at from about 0.1% to about 5%, by weight of the support, preferably from about 0.1% to about 1%, by weight. If desired, the Group VIII noble metal catalyst can contain other metals which are ordinarily used with catalyst of this type. Examples of other such metals which can be contained in such a catalyst include tin, titanium, germanium, rhenium, silicon, lead, phosphorus, arsenic, antimony, bismuth, copper, silver, cobalt, or mixtures thereof.

In accordance with the present invention, the aforementioned type of supported hydrodechlorination catalyst, which is generally known to persons of ordinary skill in the art, is treated with a non-elemental halide compound which is not a mineral acid. In other words, the present invention excludes the use of chlorine or hydrochloric acid such as shown in the aforementioned U.S. Pat. No. 5,105,032 to M. T. Holbrook et al. Examples of suitable compounds which can be used in accordance with the present invention include the alkaline metal halides, including ammonium halide, the alkaline earth metal halides, and the halogenated hydrocarbons. In such compounds, it is most preferred that the halogen atom be chlorine so that the compounds would be selected from the alkaline metal chlorides, including ammonium chloride, the alkaline earth metal chlorides, and the chlorinated hydrocarbons. Generally speaking, the treatment of the supported catalyst can take place at temperatures ranging from about 100° C. to about 500° C., preferably from about 200° C. to about 400° C. for a sufficient length of time, for instance, from about five minutes to about twenty-four hours, preferably from about thirty minutes to about four hours in order to effect the desired degree of enhancement in the durability of the catalyst.

The previously described treatment procedure also affects the morphology of the conventional "egg-shell" type hydrodechlorination catalyst (which is compared to a conventional homogeneous distribution-type catalyst in schematic FIGS. 1 and 1A in two major ways. The first is the conversion of the metal from a +1 formal valence state to the zero valence state, as determined by X-ray photoelectron spectroscopy. The second is a particle size growth of the metal species so that a predominant amount of such particles are visible under a microscope having a resolution of about 5 Å since they are predominantly in the particle size range of from about 10 Å to about 200 Å.

As is demonstrated in some of the Examples which follow, the reactant feed can either comprise hydrogen and carbon tetrachloride alone, or those reagents along with one or more gases that are inert to the desired reaction, such as gaseous HCl, helium, nitrogen and/or methane. In order to achieve the most desirable performance characteristics for the treated catalyst in the desired hydrodechlorination reaction it is preferred: to avoid overheating of the catalyst during the reaction; to avoid using a hydrogen to carbon tetrachloride ratio which is too low; and to allow for the presence of liquid condensation in the reactor.

The foregoing invention is further illustrated by the Examples which follow.

Comparative Example 1

This Example illustrates the performance of an untreated catalyst as a comparison to the results obtained from use of the present invention.

The hydrodechlorination of $CCl_4$ was performed in the vapor phase using a Johnson Matthey 0.3% $Pt/Al_2O_3$ pelletized catalyst, having a Cl content of about 0.3%, at 90° C., 1200 $hr^{-1}$, 13% $CCl_4$ in $H_2$, and one atmosphere. The catalyst was activated in hydrogen atmosphere at 350° C. for two hours before it was cooled to 90° C. at which the reaction gas mixture was introduced. It showed an initial $CCl_4$ conversion of 85%. The $CCl_4$ conversion dropped to 2% within one hour.

Comparative Example 2

This Example also illustrates the performance of an untreated catalyst as a comparison to the results obtained from use of the present invention.

A Degussa 0.3% $Pt/Al_2O_3$ catalyst was used at the same pretreatment and reaction conditions as specified in Comparative Example 1. The catalyst had a initial $CCl_4$ conversion of 18%, and the conversion dropped to 2% within one hour.

EXAMPLE 3

The deactivated Degussa 0.3% $Pt/Al_2O_3$ catalyst from Comparative Example 3 after four hours showing 2% conversion at 90° C. was activated at 200° C. in a reaction gas mixture of 13% $CCl_4$ in hydrogen. The conversion of $CCl_4$ was over 95%. After two hours, the temperature was lowered to 90° C., and the reaction was continued. The $CCl_4$ conversion was maintained at above 45% for five hours. Although this catalyst showed deactivation, the rate of deactivation was much slower than for the catalyst used in Comparative Example 2.

EXAMPLE 4

A Johnson Matthey 0.3% $Pt/Al_2O_3$ pelletized catalyst from the same batch as used in Comparative Example 1 was activated at 350° C. in hydrogen for two hours. It was then cooled to 200° C. at which 13% $CCl_4$ in hydrogen was introduced. The conversion of $CCl_4$ was over 95%. After two hours, the temperature was lowered to 90° C., and the reaction was continued. The conversion was maintained at above 40% for four hours. Although this catalyst showed deactivation, the rate of deactivation was also much slower than for the catalyst used in Comparative Example 1.

EXAMPLE 5

A Johnson Matthey 0.3% $Pt/Al_2O_3$ pelletized catalyst from the same batch as used in Comparative Example 1 was washed with a saturated solution of $NH_4Cl$. It was then dried in air at room temperature followed by activation at 350° C. in hydrogen for two hours. Subsequently, it was cooled to 90° C. at which the reactant gas mixture of Example 4 was introduced. This catalyst displayed a $CCl_4$ conversion of 85% for three days without deactivation. The selectivity for $CHCl_3$ was 80% with the balance being methane. No heavy by-products were detected.

EXAMPLE 6

A Degussa 0.3% $Pt/Al_2O_3$ pelletized catalyst from the same batch as used in Example 4 was washed with a saturated solution of $NH_4Cl$. It was then dried in air at room temperature followed by activation at 350° C. in hydrogen for two hours. It was subsequently cooled to 90° C., at which time, the reactant gas mixture of Example 4 was introduced. This catalyst displayed a $CCl_4$ conversion of 85% for seven days without deactivation. The selectivity for $CHCl_3$ was 80% with the balance being methane. No heavy by-products were detected.

EXAMPLE 7

A Johnson Matthey 0.3% $Pt/Al_2O_3$ pelletized catalyst from the same batch as used in Comparative Example 1 was washed with a saturated solution of LiCl. It was then dried in air at room temperature followed by activation at 350° C. in hydrogen for one and one half hours. Subsequently, it was cooled to 90° C. at which time the reactant gas mixture of Example 4 was introduced. This catalyst displayed a $CCl_4$ conversion of 91–95% for seven days without deactivation. The selectivity for $CHCl_3$ was 70% with the balance being methane. No heavy by-products were detected.

EXAMPLE 8

A Johnson Matthey 0.3% $Pt/Al_2O_3$ pelletized catalyst from the same batch as used in Comparative Example 1 was crushed to smaller pellets. The interior $Al_2O_3$ of the original pellet was exposed. The crushed catalyst was more rapidly deactivated than the uncrushed pellets, indicating that untreated $Al_2O_3$ was not desired for the reaction. Another batch of crushed pellets was washed with a saturated solution of $NH_4Cl$. It was then dried in air at room temperature followed by activation at 350° C. in hydrogen for two hours. Subsequently, it was cooled to 90° C. at which time the reactant gas mixture of Example 4 was introduced. This catalyst displayed a $CCl_4$ conversion of over 90% for seven days without deactivation, at a selectivity of over 70% to $CHCl_3$. The selectivity for $CHCl_3$ increased with decreasing conversion; the $CCl_4$ conversion was lowered by lowering the reaction temperature. The selectivity to $CHCl_3$ was over 80% between conversion of 20–70%.

EXAMPLE 9

A Johnson Matthey 0.3% $Pt/Al_2O_3$ pelletized catalyst from the same batch as used in Comparative Example 1 was washed with a saturated solution of $NH_4Cl$. It was then dried in air at 80° C. followed by activation at 320° C. in hydrogen for three hours. Subsequently, it was cooled to 90° C. at which the reactant gas mixture of Example 4 was introduced. This catalyst displayed a $CCl_4$ conversion of 85% for three days without deactivation. The selectivity for $CHCl_3$ was 80% with the balance being methane.

EXAMPLE 10

A Johnson Matthey 0.3% $Pt/Al_2O_3$ "egg-shell" catalyst, as received from the manufacturer, was reduced in hydrogen for two hours. This catalyst is referred to herein as the "untreated catalyst". Analysis of this untreated catalyst by X-ray photoelectron spectroscopy (XPS) indicated that the platinum content on this untreated catalyst had a +1 oxidation state. Investigation of this catalyst with transmission electron microscopy (TEM) indicated that most of the platinum particles were invisible, although some visible platinum particles were of a size that was about 2 nm.

The foregoing type of untreated catalyst was treated with a saturated solution of $NH_4Cl$. Analysis by XPS indicated that the platinum content on this untreated catalyst had a 0 oxidation state, which was indicative of platinum being in the metallic state. Analysis by TEM indicated that most of the platinum particles were of a size that was about 8 nm. The Cl content of this catalyst was about 1.5%.

EXAMPLE 11

As depicted in the Figure, the catalyst was run in a durability test at a $H_2/CCl_4$ ratio of about 6, although, as indicated below, it was lower on hot days when an operating problem occurred. The carbon tetrachloride conversion was 74% with the selectivity for $CHCl_3$ being 80% in the final analysis taken. Despite them any disturbances due to sampling and temperature fluctuation, the durability was judged to be excellent. During the test it was intended to maintain the carbon tetrachloride bath temperature at 24° C. in order to maintain the $H_2/CCl_4$ ratio given above. Since the first water bath in the experimental setup did not have refrigeration, its temperature rose to 28° C., or possibly even higher, after thirty-two days on stream. The $H_2/CCl_4$ ratio decreased to about 4.5 at this temperature which caused a decreased activity. This problem lasted for over a week before a refrigerated circulation bath was placed in the setup. Despite this problem, it should be noted that the catalyst still had a steady performance during that period of decreased activity. The activity recovered to the previous level after the problem was solved. Several cold days followed which caused some fluctuation in conversion.

EXAMPLE 12

A Johnson Matthey 0.3% Pt/alumina ⅛ inch pelleted catalyst was treated with a saturated solution of ammonium chloride. It was then dried in air at 80° C. One gram of the treated catalyst was loaded into a glass reactor where it was activated at 320° C. in hydrogen for three hours. The catalyst bed was subsequently cooled to 90° C. at which point a reactant mixture of carbon tetrachloride in hydrogen was introduced. The net flow of carbon tetrachloride vapor was at 3.5 ml/minute, and the hydrogen flow rate was 22 ml/minute. The reaction was carried out for 75 hours. The carbon tetrachloride conversion was maintained at over 80% with a selectivity to $CHCl_3$ of over 70%. Gaseous HCl was then added to the reaction mixture at flow rates of 5, 8, 10, 13, and 15 ml/minute, in stepwise increments. The conversion decreased to 50% at 15 ml/minute added HCl, and the selectivity to $CHCl_3$ was increased to 83%. The catalyst performance was stable under the high HCl flow for fifteen hours, when the test was terminated.

EXAMPLE 13

This Example used the same procedure as described in Example 12 with added HCl at 15 ml/minute in the feed at a temperature of 120° C. The carbon tetrachloride conversion was 64% with the selectivity to $CHCl_3$ being 82%. At 130° C. the carbon tetrachloride conversion was 74% with the selectivity to $CHCl_3$ being 80%.

EXAMPLE 14

The same catalyst used in Example 12 was treated, dried, loaded into a reactor, and activated as described in that Example and the catalyst bed was similarly cooled to 90° C. at which point the same reactant mixture of carbon tetrachloride in hydrogen was introduced. The reaction was, however, carried out for one hundred twenty-eight hours. The carbon tetrachloride conversion was also maintained at over 80% with a selectivity to $CHCl_3$ of over 70%. Helium was then added to the reaction mixture such that the total flow rate of hydrogen and helium was maintained at 22 ml/minute. The helium/hydrogen ratio was increased to 1/1 in the reaction feed. The catalytic carbon tetrachloride conversion and selectivity to $CHCl_3$ were not affected during a five hour test period.

Comparative Example 15

This Example illustrates the results achieved in duplicating the chloride pretreatment technique taught in U.S. Pat. No. 5,105,032 to M. T. Holbrook et al.

A Johnson Matthey 0.3% $Pt/Al_2O_3$ ⅛" pelleted catalyst (1.0 gram) was dried at 200° C. in nitrogen before cooling to 100° C. at which temperature a dry gas mixture of hydrogen (20 ml/min) and hydrogen chloride (20 ml/min) was passed through the catalyst bed. The HCl was used as the chloride pretreatment reagent in accordance with the teaching of the Holbrook et al. patent. The catalyst bed temperature was then slowly increased to 200° C. and was held at this temperature for two hours in the mixed gas flow. The hydrodechlorination reaction was started by cooling to 100° C. under hydrogen with the ratio of hydrogen to carbon tetrachloride during the reaction being maintained at 7:1. The conversion of CCl$_4$ decreased from 98% to 32% in less than an hour, and the CHCl$_3$ selectivity slightly increased from 59% to 66%.

This procedure was then repeated, and HCl was found to have little effect on the performance of the Johnson Matthey catalyst.

The foregoing Examples, which are presented for illustrative purposes only, should not be construed in a limiting sense. The scope of protection sought is set forth in the claims which follow.

I claim:

1. A process for enhancing the durability of a supported noble metal hydrodechlorination catalyst, as measured by a later hydrodechlorination reaction, which process comprises treating the supported catalyst, which comprises support and catalytic noble metal, with a non-elemental halide compound, which is not a mineral acid.

2. A process as claimed in claim 1 wherein the support is an oxidic support.

3. A process as claimed in claim 1 wherein the noble metal is a Group VIII noble metal.

4. A process as claimed in claim 1 wherein the noble metal is selected from the group consisting of platinum and palladium.

5. A process as claimed in claim 1 wherein the support is an oxidic support and the noble metal is selected from the group consisting of platinum and palladium.

6. A process as claimed in claim 1 wherein the halide is contained in a chlorinated hydrocarbon.

7. A process as claimed in claim 1 wherein the halide is contained in an alkali metal chloride.

8. A process as claimed in claim 1 wherein the halide is contained in an alkaline earth metal chloride.

9. A process as claimed in claim 5 wherein the halide is contained in a chlorinated hydrocarbon.

10. A process as claimed in claim 5 wherein the halide is contained in an alkali metal chloride.

11. A process as claimed in claim 5 wherein the halide is contained in an alkaline earth metal chloride.

12. An improved hydrodechlorination catalyst formed the process of claim 1.

13. An improved hydrodechlorination catalyst formed the process of claim 5.

* * * * *